(12) United States Patent
Kawai et al.

(10) Patent No.: US 7,029,653 B1
(45) Date of Patent: Apr. 18, 2006

(54) METHOD OF THE ADMINISTRATION OF DRUGS HAVING BINDING AFFINITY WITH PLASMA PROTEIN AND PREPARATION TO BE USED IN THE METHOD

(75) Inventors: Keiichi Kawai, Kanazawa (JP); Norito Takamura, Miyazaki (JP); Ryuichi Nishii, Beppu (JP)

(73) Assignee: Nihon Medi-Physics Co., Ltd., Hyogo (JP)

( * ) Notice: Subject to any disclaimer, the term of this patent is extended or adjusted under 35 U.S.C. 154(b) by 422 days.

(21) Appl. No.: 10/018,745

(22) PCT Filed: Jun. 21, 2000

(86) PCT No.: PCT/JP00/04039

§ 371 (c)(1),
(2), (4) Date: Dec. 21, 2001

(87) PCT Pub. No.: WO00/78352

PCT Pub. Date: Dec. 28, 2000

(30) Foreign Application Priority Data

Jun. 21, 1999 (JP) .................................. 11-173514

(51) Int. Cl.
*A61K 49/00* (2006.01)
(52) U.S. Cl. ..................... 424/9.1; 424/1.69; 424/1.11; 424/1.65; 424/9.2
(58) Field of Classification Search ............... 424/1.11, 424/1.65, 1.69, 9.1, 9.3, 9.4, 9.5, 9.6, 9.7, 424/9.8; 206/223, 569, 570; 534/7, 10–16
See application file for complete search history.

(56) References Cited

U.S. PATENT DOCUMENTS

| 4,642,284 | A | | 2/1987 | Cooper et al. |
|---|---|---|---|---|
| 4,976,950 | A | | 12/1990 | Simon et al. |
| 5,792,444 | A | | 8/1998 | Fischman et al. |
| 5,977,163 | A | * | 11/1999 | Li et al. ..................... 514/449 |

FOREIGN PATENT DOCUMENTS

| DE | 196 48 629 A | 5/1998 |
|---|---|---|
| WO | WO 98/39037 A | 9/1998 |

OTHER PUBLICATIONS

Somogyi et al (1981), British Journal of Clinical Pharmacology, vol. 12, pp. 51-60.*
English Abstract, abstracting DE 196 48 629, May 14, 1998.
Mason et al, "In-Vitro Displacement of Indomethacin from Plasma Protein Binding By Ibuprofen Phenyl Butazone and Salicylate", Univ. of Otago Medical School, vol. 52, No. 3, pp. 49-50 XP009000051 (1974).
Pritchard et al, "Plasma Protein Binding of Bepridil", Journal of Clin. Pharm., vol. 25, No. 5, pp. 347-353 XP001083994 (1985).
Bertucci C et al, "The binding of 5-fluorouracil to native and modified human serum albumin: UV, CD and 1H and 19F NMR investigation", Journal of Pharm. and Bio. Analysis, vol. 13, No. 9, XP002101869 (1995).
Kawai, K. et al., Compeittive displacement of 99mTc-MAG3 serum protein binding in in-vitro and in-vivo.:, Journal of Labelled Compounds and Radiopharmaceuticals, Jun. 1999, vol. 42, SUPPL. 1, pp. S584-S-586.
Bubeck, Berand et al., Pharmacokinetics of Technetium -99m-MAG3 in Humans.:, The Journal of Nuclear Medicine, 1990, vol. 31, No. 8, pp. 1285-1293.
Matsui, Mieko et al., "Application of fractional uptake method to 99mTc-ECD SPECT for quantification of brain perfusion using cardiac output index.", Kobe Daigaku Igakubu Kiyo, 1998, vol. 58, No. 4, pp. 191-196, Abstract.
Ivarsen, Per Ramloev et al., "Displacement of bilirubin from adult and newborn serum albumiun by a drug and fatty acid.", Dev. Pharmacol. Ther., 1989, vol. 12, No. 1, pp. 19-29.
Briand, C. et al., "Study of the interaction between human serum albumin and some cephalosporins.", Mol. Pharmacol. 1982, vol. 21, No. 1, pp. 92-99.
Semmes, Robin L.O. et al., Nonlinear binding of valproic acid (VPA) and E-Δ2-valproic acid to rat plasma proteins.:, Pharm. Res. 1990, vol. 7, No. 5, pp. 461-467.
Lockwood, Graham F. et al., "Pharmacokinetics of ibuprofen in man-III: Plasma protein binding.", J. Pharmacokinet. Biopharm. 1983, vol. 11, No. 5, pp. 469-482.
Abdel-Rahman M. et al., "Interaction between verapamil and vincristine binding to plasma proteins.", International Journal of Clinical Pharmacology, Therapy, and Toxicology, 1992, vol. 30, No. 11, pp. 536-537.

* cited by examiner

*Primary Examiner*—Dameron L. Jones
(74) *Attorney, Agent, or Firm*—Sughrue Mion, PLLC

(57) ABSTRACT

A method of the administration of drugs with binding affinity for plasma protein and drugs regulating the effective ingredient dose of drugs with binding affinity for plasma protein; and a preparation whereby the effective ingredient dose of drugs with binding affinity for plasma protein is regulated. The above administration method is characterized in that, in the administration of a first drug having binding affinity for plasma protein, a second drug having binding affinity for the same plasma protein is administered simultaneously with the first drug or before or after the administration of the first drug to thereby regulate the binding of the first drug to the plasma protein.

13 Claims, 4 Drawing Sheets

METHOD OF THE ADMINISTRATION OF DRUGS HAVING BINDING AFFINITY WITH PLASMA PROTEIN AND PREPARATION TO BE USED IN THE METHOD

TECHNICAL FIELD

The present invention relates to a method of the administration of drugs with binding affinity for plasma protein and drugs regulating the effective ingredient dose of drugs with binding affinity for plasma protein; and a pharmaceutical preparation whereby the effective ingredient dose of drugs with binding affinity for plasma protein is regulated.

BACKGROUND ART

Generally, drugs administered for the purpose of medical treatment or diagnosis once go through the systemic blood circulation, and then take the process of absorption, distribution, metabolism, excretion and the like. In the process of absorption and distribution, the drug moves along on flow of the blood, while it transfers to each spaces of intravascular, interstice and intracellular by diffusion and transportation of a free drug being in the state of unbound form with proteins, and finally the drug arrives at the active region of target. When movement of the drug reaches a steady state, then the free drug concentration in each space become uniform, thus the whole pattern of the concentration of the drug is determined by the binding level with proteins. Hence, in accordance with the property, a drug in vivo, may partially exists in the form of reversible binding state with biopolymers such as plasma proteins. Generally, drugs permeable through capillary wall or cell membrane are free drugs, therefore, the transfer of such free drugs being unbound with plasma proteins to the active region of target may be greatly influenced by the binding level with plasma proteins.

For example, mercaptoacetylglycylglycylglycine labeled with 99m-technetium ($^{99m}$Tc-MAG$_3$) is widely used in renal scintigraphy, especially the renal plasma flow can be effectively exhibited by its efficient renal extraction and renal tubular secretion. It is known that about 90% of $^{99m}$Tc-MAG$_3$ binds to plasma protein in an ordinary clinical dose (Bubeck B. et al., J. Nucl. Med., 31, 1285–1295, 1990). If the binding of $^{99m}$Tc-MAG$_3$ with plasma protein is inhibited by drugs having high binding affinity to the same binding site on protein with $^{99m}$Tc-MAG$_3$, then more clear renal imaging can be obtained in the earlier stage after the administration, thus it may be thought that the dose of radioactivity to the patient can be reduced at the same time.

On the contrary, if the binding of drugs with plasma protein is increased, then the concentration of the free drugs in the blood can be kept in lower level for long period, therefore, it may be possible to achieve continuous appearance of pharmacological effects.

However, at the present stage, little is known as the research work for improving therapeutic effect or diagnostic effect of the drugs by regulating the concentrations of the free drugs, using the binding affinity of the second drug with plasma proteins.

DISCLOSURE OF THE INVENTION

In consideration of the above-mentioned problems, an object of the present invention is to provide a suitable method of the administration of drugs by regulating the binding affinity of the drug for plasma proteins, and at the same time, to provide a pharmaceutical preparation whereby the binding affinity of the drug for plasma protein can be regulated.

According to the present invention, the suitable administration of the drugs can be achieved by regulating the binding affinity of the drug for plasma protein, and at the same time, a pharmaceutical preparation for such administration can be provided.

The present invention relates to a method of administration of drugs with binding affinity for plasma protein, characterized by regulating the binding affinity of the first drug for plasma protein, when administering the first drug with the binding affinity for plasma protein, the second drugs, which have the binding affinity for the same plasma protein, for which the first drug has binding affinity, is administered simultaneously with the first drug or before or after the administration of the first drug.

Particularly, in the case of regulating the binding affinity of the first drug for plasma protein, it is preferable that the first drug and the second drugs bind to the same binding sites on the plasma protein. Further, the second drug may be administered before, after or simultaneously with the administration of the first drug, and such administration timing of the second drug can be suitably selected in connection with the timing when the free drug concentration of the first drug reaches to the level so as to obtain an adequate effect. Additionally, a single drug may be used as the second drug, or plural drugs may be used as the second drugs when synergistic effect can be expected.

In case of administering the first drug and the second drug simultaneously, the pharmaceutical preparations comprising the first drug and the second drug may be supplied. Further, the first drug and the second drug may be filled in a container separately, and may be supplied as a kit form. In case of such a kit form with separate containers, they may be administered simultaneously by mixing it together when used, or each one of the first drug and the second drug can be administered in different times separately or by different route. Furthermore, both of or either one of these first and second drugs may be commercially available pharmaceuticals.

When the first drug is radiodiagnosic agent for in vivo use or radiotherapeutic drug for in vivo use, the radioactive nuclides can be selected from the group comprising 11-carbon ($^{11}$C), 15-oxygen ($^{15}$O), 18-fluorine, ($^{18}$F), 32-phosphorus ($^{32}$P), 59-iron ($^{59}$Fe), 67-copper ($^{67}$Cu), 67-gallium ($^{67}$Ga), 81m-krypton ($^{81m}$Kr), 81-rubidium ($^{81}$Rb), 89-strontium ($^{89}$Sr), 90-yttrium ($^{90}$Y), 99m-technetium ($^{99m}$Tc), 111-indium ($^{111}$In), 123-iodine ($^{123}$I), 125-iodine ($^{125}$I), 131-iodine ($^{131}$I), 133-xenon ($^{133}$Xe), 117m-tin ($^{117m}$Sn), 153-samarium ($^{153}$Sm) 186-rhenium ($^{186}$Re), 188-rhenium ($^{188}$Re), 201-thallium ($^{201}$Tl), 212-bismuth ($^{212}$Bi), 213-bismuth ($^{213}$Bi) and 211-astatine ($^{211}$At).

In this case, compounds, such as chelating group or receptor ligand, of the first drug labeled with the above-mentioned nuclides can be selected from bisaminothiol or its derivatives, monoaminomonoamidobisthiol or its derivatives, bisamido-bisthiol or its derivatives, mercaptoacetylglycylglycyl-glycine or its derivatives, hexamethylpropyleneamineoxime or its derivatives, ethylenebis[bis(2-ethoxyethyl)phosphine](tetrofosmin) or its derivatives, 2,3-dimercaptosuccinic acid or its derivatives, ethylenecysteine dimer derivatives, methoxyisobutylisonitrile derivatives, polyamine derivatives, pyridoxylydeneaminate derivatives, methylene diphosphonate, hydroxymethylene diphodphonate derivatives, β-methyl-ω-phenylpentadecanoic acid or its derivatives, N-isopropyl-amphetamine, hippuric acid, benzylguanidine, tropane derivatives and the like.

The second drug may be selected from, for example, bucolome, cefazolin, etoposide, phenylbutazone, aspirine, salicylic acid, cefatriaxone, sulfamethizole, valproic acid, nabumetone, 6-methoxy-2-naphtyl acetic acid, ibuprofen, probenecid, dansyl-L-asparagine (DNSA), verapamil or disopyramide and the like.

BEST MODE FOR CARRYING OUT OF THE INVENTION

Figure 1:
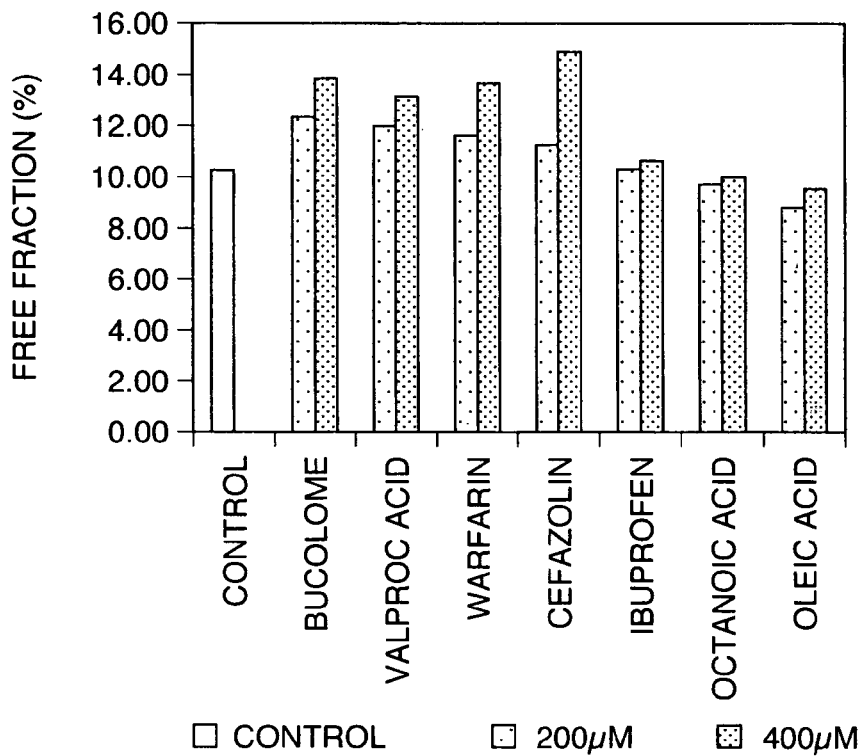
FIG. 1 shows the free fraction of $^{99m}$Tc-MAG$_3$ in human plasma in the presence of site specific agent.

When the second drug having high binding affinity for the same plasma protein, for which the first drug has binding affinity, is administered simultaneously with the first drug, or before or after the administration of the first drug, then competitive displacement will take place at the binding site, thus it can be thought that the first drug may be released in a higher concentration (displacement effect). Therefore, it can be expected that the higher pharmacological activity of the first drug can be obtained as compared with the case that the first drug is administered singly. On the contrary, when the binding fraction of the first drug to plasma protein increases by the effect of the second drug (reducing effect of the free drug concentration), continuous appearance of pharmacological effect of the first drug can be expected to achieve by keeping the free fraction of the first drug in blood at a lower level for long period.

In the present invention, the first drug with binding affinity for plasma protein may be either one of therapeutic agent or diagnostic agent, as long as it meets the purpose of administration.

Regardless of therapeutic or diagnostic purpose, in case of obtaining the above-mentioned displacement effect, the second drug may be preferably selected from those having competitive binding affinity for the same plasma protein as the first drug has; increasing the free fraction of the first drug by the binding inhibition of the first drug with plasma protein; having the affinity for the same binding site of the first drug on plasma protein; and having the higher binding affinity for plasma protein.

On the contrary, in case of obtaining the above-mentioned reducing effect of the free drug concentration, the object is achieved by selecting the second drug from those having effect to increase the binding affinity of the first drug for plasma protein by the second drug bound to the same plasma proteins.

At the present, a report relating to research for clarifying the entity of the reducing effect of the free drug concentration has not been found yet. While, it can be considered that said reducing effect may appear, for example by a mechanism similar to the allosteric effect of an enzyme, and surprisingly, it was found that the binding affinity for the plasma protein could be increased by using the combination of the drugs shown in Example 8 of the present invention.

Regarding dose forms of the drug, in the case that the first drug and second drug are administered simultaneously without necessarily considering any chemical change such as decomposition thereof by mixing together, it is possible to supply a pharmaceutical product prepared by mixing the first drug with the second drug. In such a mixed-type of pharmaceutical preparation, medicinally acceptable ingredients, such as pH-adjusting agents, inorganic salts for adjusting the osmotic pressure, stabilizing agents for stabilizing each one of these ingredients may be added thereto. The mixed-type of pharmaceutical preparations can be processed into the suitable dose form, for example a liquid form preparation, a lyophilized form preparation and the like, in consideration of the constitutional ingredients, preservation stability thereof, etc. Further, the first drug and the second drug may be supplied as a kit form in which they are filled in a container separately. Similar to the mixed-type preparation, medicinally acceptable ingredients, such as stabilizing agents or the like may be added to each one of these separate type of drugs, and in consideration of administeration method, stabilization and the like, these separate type of the drugs can be processed into the suitbale form of preparations, such as liquid form preparation, a lyophylized form preparation and the like.

In case of the kit form mentioned above, the first drug and the second drug can be administered separately, or can be administered simultaneously by mixing together at the time of use. Especially, in the case of predicting changes of quality of the product, such as decomposition of the ingredients during the storage after mixing the first drug and the second drug, and in the case that these drugs are administered by different route, or in the case that these drugs are administered necessarily in different timings, the abovementioned kit form in which the first drug and the second drugs are filled in separate containers are useful.

Generally, as the plasma proteins bound to drug, human serum albumin (HSA), $\alpha_1$-acidic glycoprotein (AGP), γ-globulin, lipoprotein and the like are exemplified, and many drugs may bind to HSA or AGP. In selecting the second drug, for example when the first drug has the property of mainly binding to HSA, it may be preferably selected from an acidic drug having the binding affinity for HSA. When the first drug has the property of binding to AGP, it may be preferably selected from a basic drug having the binding affinity for AGP. Further, in the case that the first drug has the affinity for plural plasma proteins or has the affinity for different binding sites on the single protein, the use of plural drugs as second drugs may be effective. Furthermore, in case of selecting the second drug, other properties than the binding affinity with the above-mentioned plasma protein should be considered, such as clinically acceptable appearance of the original pharmacological activity, a broad range of usual dose, and maintenance of high blood concentration after administration, etc.

Administration timing of the second drug may be either simultaneously with the first drug or before or after the administration of the first drug, thus the timing is selected suitably so as to obtain the effect to meet the administration purpose of the first drug. Administration route of the drugs may be suitably selected from either one of intravenous injection, intraarterial injection, subcutaneous injection, lymphaginal injection or oral administration.

Specifically, HSA has three specific binding sites such as site I, site II and site III on its molecule. As the second drug with binding specificity at the site I, the following drugs can be exemplified; bucolome (5-n-butyl-1-cyclohexyl-2,4,6-trioxoperhydropyrimidine), cefazolin (7-[1-(H)-tetrazolylacetamido]-3-[2-(5-methyl-1,3,4-thiazolyl)thiomethyl]-3-cephem-4-carboxylate), phenylbutazone (1,2-diphenyl-3,5-dioxo-4-n-butyl-pyrazolidine), valproic acid (sodium 2-propylpentanoate), aspirin (2-acetoxybenzoic acid), salicylic acid (O-hydroxybenzoic acid), ceftriaxone (disodium (6R,7R)-7-[2-amino-4-thiazoyl]-2-methoxyiminoacetamide)-3-(2,5-dihydro-2-methyl-6-oxide-5-oxo-1,2,4-triazin-3-ylthiomethyl)-8-oxo-5-thia-1-azobicyclo[4.2.0]octo-2-ene-2-carboxylate), sulfamethizol (N-(5-methyl-1,3,4-thiadiazol-2-yl)sulfanylamide), canrenoic acid (17-hydroxy-3-oxo-17α-pregna-4,6-dien-21-carboxylate), dansyl-L-asparagine, etc. As the second drug with binding specificity at the site II, the following drugs can be exemplified; ibuprofen (2-(4-isobutylphenyl)propionic acid), nabumetone (4-(6-methoxy-2-naphthyl)-2-butanone (6-methoxy-2-naphthylacetic acid, which is a metabolite of nabumetone, shows binding specificity at the site II) and probenecid (4-(N,N-dipropylsulfamoyl)benzoic acid), etc. Further, etoposide ((5S, 5aR, 8aR, 9S)-9-[(4,6,O-(R)-ethylidene-β-D-glucopyranosyl)oxy]-5,8,8a,9-tetrahydro-5-(4-hydroxy-3,5-dimethoxyphenyl-isobenzofuro[5,6-f][1,3]benzodioxol-6 (5aH)-one) also has binding specificity for HSA, though the binding site on the HSA has not been assigned. As the second drug with binding specificity for AGP, the following drugs can be exemplified, disopyramide (α-(2-diisopropylaminoethyl)-α-phenyl-2-pyridineacetamide), verapamil (α-[[2-(3,4-dimethoxyphenyl)ethyl]-methylamino]propyl]-3,4-dimethoxy-α-(1-methylethyl)benzeneacetonitrile) and propranolol(1-isopropylamino-3-(1-naphthyloxy)-2-propanol), etc.

As compounds, such as chelating group or recetor ligand, of radio-therapeutic drug for in vivo use or radiodiagnostic drug for in vivo use, both having binding affinity for plasma protein and being labeled with radioactive nuclides, following compounds can be exemplified; mercaptoacetylglycylglycylglycine ($MAG_3$) or its derivatives, hexamethylpropyleneaminoxime(HMPAO) or its derivatives, ethylenebis[bis (2-ethoxyethyl)phosphine] (tetrofosmin) or its derivatives, 2,3-dimercaptosuccinic acid (DMSA) or its derivatives, ethylene cysteine dimer (ECD) derivatives such as N,N'-ethylene-L-cystein diethylester and the like, methoxyisobutyl-isonitrile (MIBI) derivatives, polyamine derivatives such as diethylenetriaminepentaacetic acid (DTPA) and the like, pyridoxylideneaminate derivatives such as pyridoxyleneisoleucine and the like; other chelating groups which can form complex with radioactive metals such as methylene diphosphonate (MDP), hydroxymethylene diphosphonate (HMDP) and the like; and compounds labeled with radioactive iodine such as β-methyl-p-iodophenylpentadecanoic acid (BMIPP), N-isopropyl-p-iodoamphetamine (IMP), iodinated hippuric acid (OIH), 3-iodobenzylguanidine (MIBG), tropane derivatives such as N-(3-fluoropropyl)-2β-carbomethoxy-3β-(4-iodophenyl)nortropane (FP-CIT), N-methyl-2β-carbomethoxy-3β-(4-iodophenyl)nortropane (CIT) and the like.

As the radioactive nuclides, following nuclides can be exemplified; 11-carbon ($^{11}C$), 15-oxygen ($^{15}O$), 18-fluorine ($^{18}F$), 32-phosphorus ($^{32}P$), 59-iron ($^{59}Fe$), 67-copper ($^{67}Cu$), 67-gallium ($^{67}Ga$), 81m-krypton ($^{81m}Kr$), 81-rubidium ($^{81}Rb$), 89-strontium ($^{89}Sr$), 90-yttrium ($^{90}Y$), 99m-technetium ($^{99m}Tc$), 111-indium ($^{111}In$), 123-iodine ($^{123}I$), 125-iodine ($^{125}I$), 131-iodine ($^{131}I$), 133-xenon ($^{133}Xe$), 117m-tin ($^{117m}Sn$), 153-samarium ($^{153}Sm$) 186-rhenium ($^{186}Re$), 188-rhenium ($^{188}Re$), 201-thallium ($^{201}Tl$), 212-bismuth ($^{212}Bi$), 213-bismuth ($^{213}Bi$) and 211-astatine ($^{211}At$). As to the diagnostic purpose, 18 -fluorine ($^{18}F$), 99m-technetium ($^{99m}Tc$), 67-gallium ($^{67}Ga$), 111-indium ($^{111}In$), 123-iodine ($^{123}I$), 131-iodine ($^{131}I$) and the like are frequently used.

Figure 5:
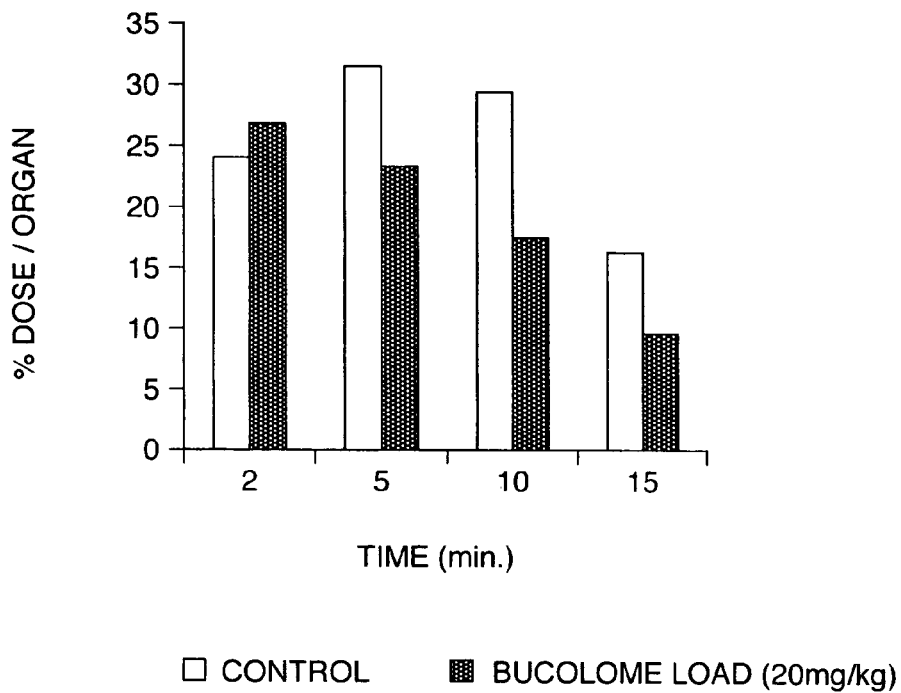
FIG. 5 shows the effect of bucolome on the accumulation of $^{99m}$Tc-MAG$_3$ in rat kidney after administration of bucolome.
Figure 6:
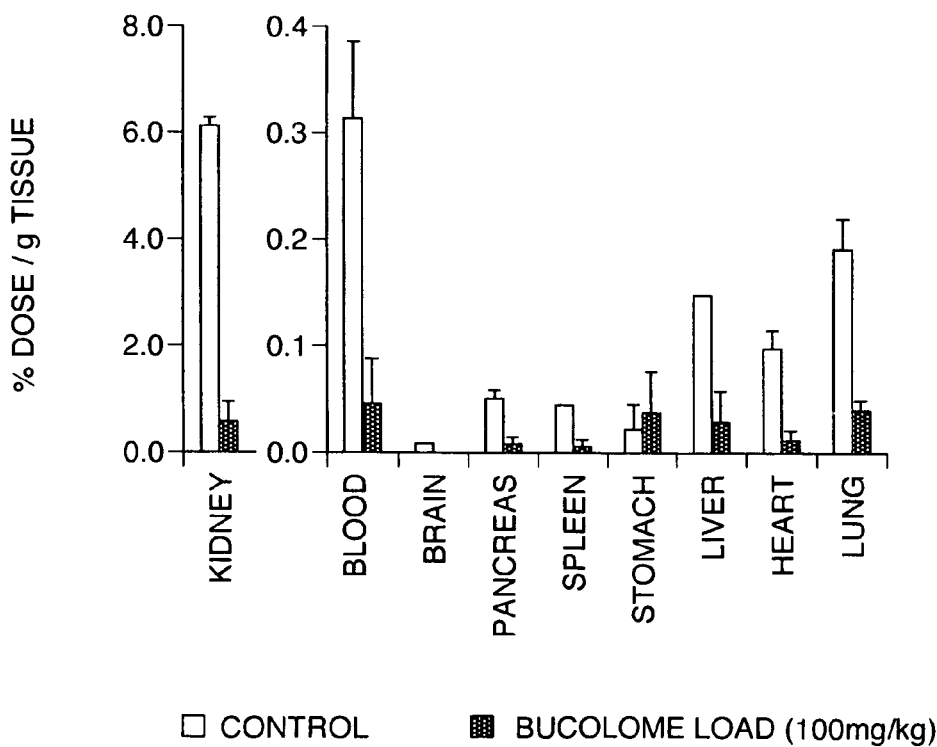
FIG. 6 shows the effect of bucolome loading on the biodistribution of $^{99m}$Tc-MAG$_3$ in rat.

99m-Technetium complex of $MAG_3$ ($^{99m}Tc$-$MAG_3$) is a radiopharmaceutical for in vivo use and is widely used for the purpose of diagnosis of renopathy and uropathy, because it possesses accumulation property to the kidney. It is known that about 90% of $^{99m}Tc$-$MAG_3$ bind to plasma protein. For this reason, in vitro study was conducted by using $^{99m}Tc$-$MAG_3$ as the first drug, the serum as the plasma protein, wherein the blood cells and blood coagulation factors are removed, and several pharmaceuticals with the binding affinity for serum proteins as the second drug. As the result, when bucolome, valproic acid, warfarin or the like was added, then displacement of $^{99m}Tc$-$MAG_3$ occurred either in human serum albumin or in rat serum albumin, thus the free fraction of $^{99m}Tc$-$MAG_3$ in serum albumin increased. In case of bucolome, the free fraction of $^{99m}Tc$-$MAG_3$ particularly increased (Table 1). FIG. 5 shows time course of accumulation of $^{99m}Tc$-$MAG_3$ in the rat kidney after administering 20 mg/kg of Bucolome. FIG. 6 shows the biodistributions in rats at 10 minutes after the administration of $^{99m}Tc$-$MAG_3$. In this case, 10 minutes before the administration of $^{99m}Tc$-$MAG_3$, 100 mg/kg of bucolome was administered. These results show that the amount of free $^{99m}Tc$-$MAG_3$ was increased by bucolome loading, and rapid clearance from the blood and accumulation of $^{99m}Tc$-$MAG_3$ into the kidney took place.

Regarding 99m-technetium complex of diethyl ester of N,N'-ethylene-L-cystein ($^{99m}Tc$-ECD), which is a radiopharmaceutical used for scintigraphy of regional cerebral blood flow, in the in vitro experiment by using a human serum, the displacement effect was observed by adding Etoposide (cf. Example 4 and Table 8).

For the purpose to prove the displacement effect on organic compounds, in vitro and in vivo experiments were conducted by using N-isopropyl-p-iodoamphetamine ($^{123}I$-IMP) as one example of organic compounds. In in vitro experiments, the displacement effects were observed by adding warfarin or 6-methoxy-2-naphthylacetic acid (6-MNA), both of which have the specificity to HSA, or by adding verapamil which has the binding specificity to AGP (cf. Example 5 and Table 9), thus the displacement effect on organic compounds was observed and proved. Further, in the experiments by using 6-MNA and Verapamil in which those were added separately or added simultaneously, the synergistic effect of the displacement effect was observed, thus it is indicated that the displacement effect can be enhanced by using plural second drugs together (cf. Example 6 and Table 10).

In in vivo experiments in rats, as compared with the control group (unloaded with verapamil), the higher concentration of free $^{123}I$-IMP in blood was observed in the test group (loaded with verapamil). Reflecting the fact, 10 minutes after the administration, the brain uptake of $^{123}I$-IMP in the test group (loaded with verapamil) was about 2 times that in the control group (Example 7). In this in vivo experiments, the test solution containig both of $^{123}I$-IMP and verapamil was prepared in advance (Example 7 (1)) and used it in the experiment. Results of Example 7 indicates that it is possible to regulate the free drug concentration by simultaneous administration of the first and second drugs using their mixture as well as by the separate administration of the first drug and the second drugs and the biodistribution of the first drug could reflect it.

As for an example of the reducing effect of the free drug concentration, decrease in the free fraction (i.e., increase in binding fraction to protein) was observed in in vitro experiment using N-(3-fluoropropyl)-2β-carbomethoxy-3β-(4-iodophenyl)-nortropane labeled with radioactive iodine (I-125) ($^{125}$I-FP-CIT) together with human serum by adding dansyl-L-asparagine (DNSA) which is specific to the site I on albumin (cf. Example 8 and Table 15).

EXAMPLES

The present invention will be explained in more detail by illustrating the following examples, but the invention will not be restricted only to these examples.

Methods for testing the compounds obtained and the reagents used are as follows.
(1) Ultrafiltration: Filtration was conducted by using an equipment of ULTRACENT-10 which treats for up to 1.5 ml (manufactured by Tosoh Corp.).
(2) $^{99m}$TcO$_4^-$: Prepared by use of a $^{99}$Mo/$^{99m}$Tc generator of MEDITECH (manufactured by NIHON MEDI-PHYSICS CO., LTD.) and used its eluent as in the form of a physiological saline solution.
(3) Reagents: The all reagents used were "Extra-pure reagent grade".
(4) Test animals: The all test animals used were Wister-strain male rats (body weight: 200–250 g). Prior to the test, the animals were breeded under light-dark cyclic condition in every 12 hours for 1 week, and had free access to food and water.

Example 1

Examination of Displacement Effects of the Second Drugs On $^{99m}$Tc-MAG$_3$ Binding to Plasma Protein Displacement test of $^{99m}$Tc-MAG$_3$ binding to serum albumin was conducted as follows by use of human serum or rat serum and site-specific drugs (second drugs) with binding affinity for the binding site I or site II on albumin. Bucolome, valproic acid, warfarin and cefazolin were used as site-specific drugs with binding affinity for the site I, and ibuprofen, sodium octanoate and sodium oleate were used as site-specific drugs with binding affinity for the site II.

First, albumin content in a normal human serum was measured previously, and the concentration of the human serum albumin (HSA) was adjusted to 500 μM by phosphate buffer (pH=7.4).

Further, a site-specific drug with the binding affinity for the site I or the site II on HSA was added to the above-mentioned serum solution, as in the form of a methanol solution or an aqueous solution. As the sample solution for control group, only methanol or water was added to the above-mentioned serum solution.

Next, a certain amount of $^{99m}$Tc-MAG$_3$ (about 740 kBq/ 20 μl) was added to each of the sample and a certain amount (20–50 μl) of the sample was taken out as the specimen before ultrafiltration. Each 0.9 mL of the samples was put in a ultrafilter and conducted ultrafiltration under the condition of 1500×g, for 10 minutes. Then, 20–50 μl each of the filtrates was taken out as the specimen after ultrafiltration. Radioactivities (cpm) of the specimens before and after ultrafiltration were measured, and the free fraction (%) of $^{99m}$Tc-MAG$_3$ was calculated by the following equation:

free fraction of $^{99m}$Tc-MAG$_3$ (%)=$[A]/[B]$

Figure 2:
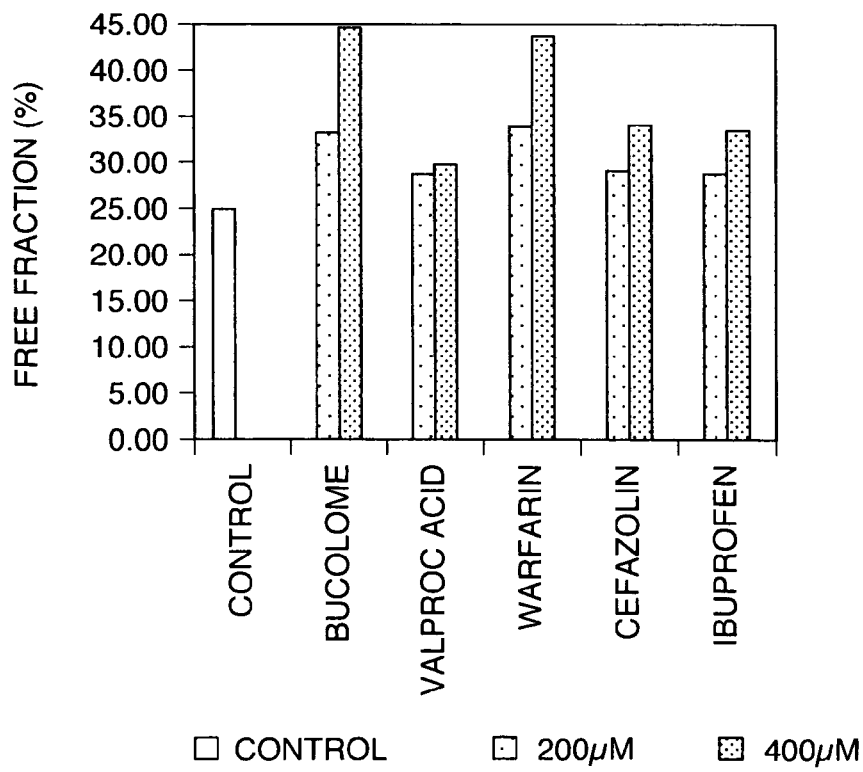
FIG. 2 shows the free fraction of $^{99m}$Tc-MAG$_3$ in rat plasma in the presence of site specific agent.

[A]: Radioactivity (cpm) after ultrafiltration,
[B]: Radioactivity (cpm) before ultrafiltration Similarly, albumin content in normal rat serum was previously measured, and the concentration of the rat serum albumin (RSA) was adjusted to 375 μM by phosphate buffer (pH=7.4) so as to conduct the test similar to that of the case of human serum. The results are shown in Table 1, FIG. 1 and FIG. 2.

In the case of human serum, the free fraction (%) of $^{99m}$Tc-MAG$_3$ in the test samples to which a site-specific drug to site I was added, such as bucolome, valproic acid, warfarin or cefazolin, was significantly increased as compared with the free fraction (10.2%) of $^{99m}$Tc-MAG$_3$ of the control sample.

On the other hand, in other test samples to which a site-specific drug to site II was added, such as ibuprofen, sodium octoate or sodium oleate, increase in the free fraction was not observed.

Similarly, in test samples of the rat serum to which a site-specific drug to site I was added, increase in the free fraction (%) of $^{99m}$Tc-MAG$_3$ was observed.

As can be seen from the above results, it is clearly indicated that the free fraction of $^{99m}$Tc-MAG$_3$ in the blood can be increased by adding a site-specific drug to site I. Although, warfarin, octanoic acid and oleic acid might be considered clinically unsuitable for the purpose of this invention, they were used for the confirmation of the effects of site-specific drugs to the binding site.

TABLE 1

Displacement effects of the second drugs on $^{99m}$Tc-MAG$_3$ binding to plasma protein

| Site-specific drug (second drug) | Human serum albumin (HAS) $^{99m}$Tc-MAG$_3$ free fraction (%) | | Rat serum albumin (RSA) $^{99m}$Tc-MAG$_3$ free fraction (%) | |
|---|---|---|---|---|
| concentration | 200 μM | 400 μM | 200 μM | 400 μM |
| Control | 10.20% | | 24.75% | |
| bucolome | 12.23% | 13.74% | 32.76% | 43.85% |
| valproic acid | 11.98% | 13.02% | 28.48% | 29.30% |
| warfarin | 11.50% | 13.57% | 33.57% | 43.28% |
| cefazolin | 11.13% | 14.76% | 28.58% | 33.52% |
| ibuprofen | 10.18% | 10.53% | 28.48% | 33.04% |
| octanoic acid | 9.60% | 9.86% | — | — |
| oleic acid | 8.74% | 9.44% | — | — |

Example 2

Biodistribution of $^{99m}$Tc-MAG$_3$ in Rat Loaded with Bucolome

Effect of second drug on biodistribution of $^{99m}$Tc-MAG$_3$ in rat was examined using the control group and the test group with bucolome loading. $^{99m}$Tc-MAG$_3$ ($^{740}$ kBq/100 μl) was administered to the tail vein of Wister-strain rat. The rats were decapitated at 2, 5, 10 and 15 minutes after administration of $^{99m}$Tc-MAG$_3$, then the blood and the organs of interest were excised. After measured the weight of these orgams, the radioactivities were determined. After decay correction of the radioactivity, the accumulation ratios (% dose/organ and % dose/g of the tissue) were determined.

As for the rat of test group loaded with bucolome, 5 minutes before the administration of $^{99m}$Tc-MAG$_3$, 20 mg/kg of body weight or 100 mg/kg of body weight of bucolome was administered to the tail vein.

The results are shown in Table 2 and Table 3 (control group), Table 4 and Table 5 (test group, loaded with 20 mg/kg of bucolome) and Table 6 (test group, loaded with 100 mg/kg of bucolome).

In the control group and test group with bucolome loading of 20 mg/kg of body weight, wherein the dose and other conditions were the same as mentioned above, except the decapitation time was prescribed at 2, 5 and 10 minutes, administrations and decapitations of rats were conducted so that 3–5 ml of blood per one rat were collected. Serum was separated using a sample tube, after that the free fraction was determined by the procedures as described in Example 1. The time course of the free fraction of $^{99m}$Tc-MAG$_3$ in vivo are shown in FIG. 4.

Figure 3:
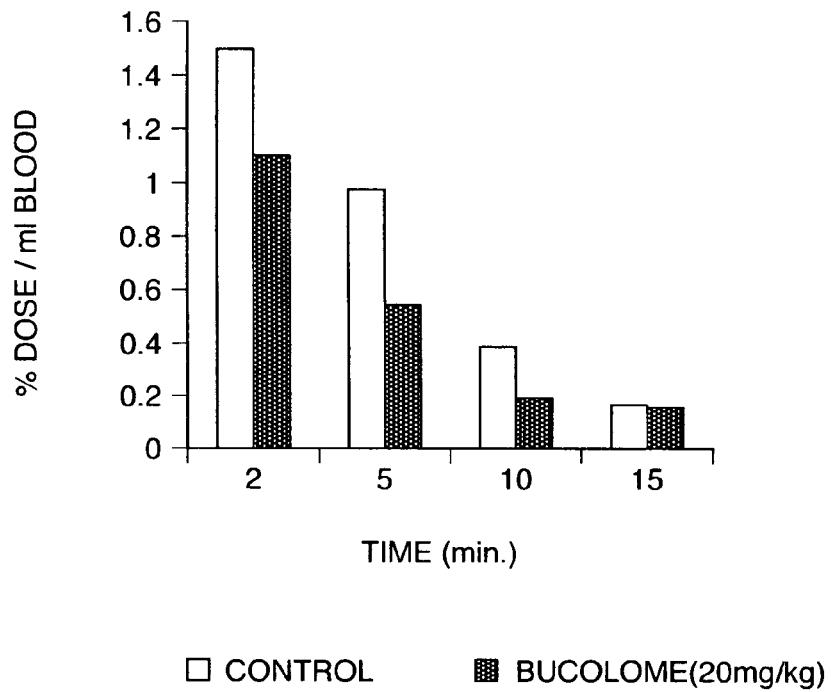
FIG. 3 shows the effect of bucolome on blood clearance of $^{99m}$Tc-MAG$_3$ in rat.
Figure 4:
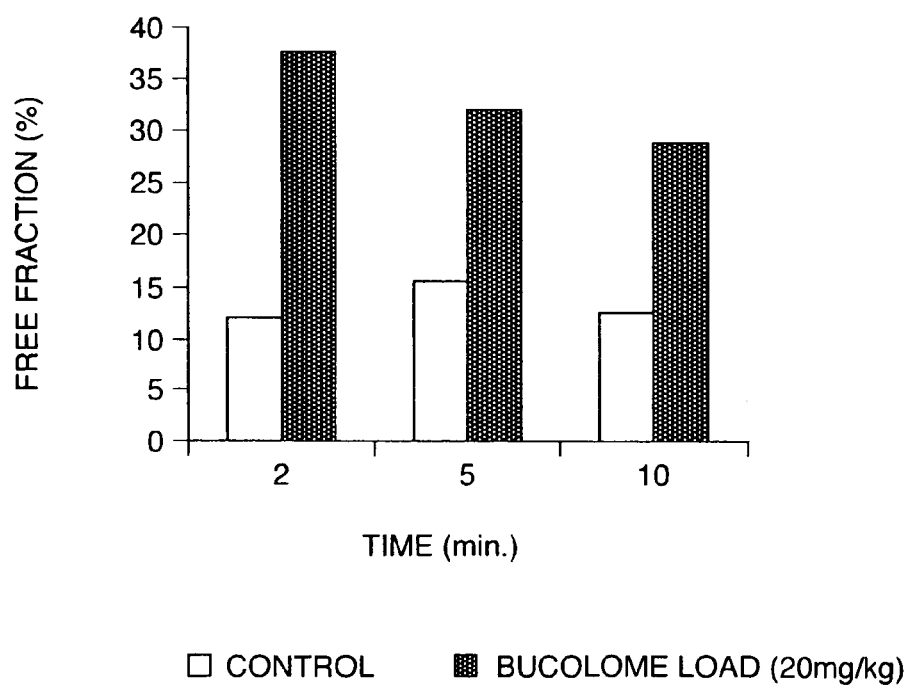
FIG. 4 shows the effect of bucolome on the free fraction of $^{99m}$Tc-MAG$_3$ in rat blood after administration of bucolome.

From the results shown above, it has become appearant that blood clearance was accelarated in the test group with bucolome loading (FIG. 3), and the free fraction of $^{99m}$Tc-MAG$_3$ in vivo in test group was remarkably increased (FIG. 4).

In the control group, accumulation of $^{99m}$Tc-MAG$_3$ in the kidney (% dose/organ) increased from 2 minutes to 5 minutes after the administration, then gradually decreased and disappeared. While, in test group with bucolome loading, accumulation of $^{99m}$Tc-MAG$_3$ in the kidney rapidly increased to the maximum value just after the administration (in 2 minutes), then decreased and disappeared quickly as compared with that of the control group (FIG. 5).

Biodistribution of $^{99m}$Tc-MAG$_3$ (% dose/g tissue) in rat 10 minutes after the administration is shown in FIG. 6. As can be seen from FIG. 6, in the test group with bucolome loading, $^{99m}$Tc-MAG$_3$ was rapidly cleared from the kidney which is the target organ of $^{99m}$Tc-MAG$_3$, thus radioactivity was quickly cleared as compared with that of the control group. Clearance from the blood and other organs were also rapid.

TABLE 2

Biodistribution of $^{99m}$Tc-MAG$_3$ in rats
(Control group: % dose/organ)

| Organs | 2 minutes | 5 minutes | 10 minutes | 15 minutes |
| --- | --- | --- | --- | --- |
| Spleen | 0.110 ± 0.024 | 0.064 ± 0.001 | 0.025 ± 0.006 | 0.014 ± 0.001 |
| Pancreas | 0.137 ± 0.026 | 0.079 ± 0.013 | 0.084 ± 0.050 | 0.030 ± 0.001 |
| Stomach | 0.276 ± 0.011 | 0.169 ± 0.003 | 0.119 ± 0.043 | 0.178 ± 0.009 |
| Liver | 5.196 ± 0.387 | 5.187 ± 2.759 | 1.671 ± 0.099 | 0.973 ± 0.266 |
| Kidney | 23.882 ± 4.669 | 31.324 ± 4.979 | 29.198 ± 3.729 | 15.864 ± 3.960 |
| Heart | 0.262 ± 0.039 | 0.184 ± 0.046 | 0.079 ± 0.028 | 0.034 ± 0.004 |
| Lung | 0.635 ± 0.116 | 0.594 ± 0.106 | 0.275 ± 0.042 | 0.129 ± 0.084 |
| Urine | 0.236 ± 0.119 | 1.309 ± 0.941 | 16.872 ± 4.042 | 38.419 ± 2.150 |

TABLE 3

Biodistribution of $^{99m}$Tc-MAG$_3$ in rats
(Control group: % dose/g tissue)

| Organs | 2 minutes | 5 minutes | 10 minutes | 15 minutes |
| --- | --- | --- | --- | --- |
| Blood | 1.482 ± 0.137 | 0.968 ± 0.163 | 0.387 ± 0.018 | 0.160 ± 0.022 |
| Spleen | 0.171 ± 0.031 | 0.104 ± 0.014 | 0.044 ± 0.008 | 0.026 ± 0.006 |
| Pancreas | 0.233 ± 0.029 | 0.150 ± 0.001 | 0.096 ± 0.027 | 0.048 ± 0.007 |
| Stomach | 0.176 ± 0.011 | 0.031 ± 0.012 | 0.015 ± 0.010 | 0.110 ± 0.050 |
| Liver | 0.579 ± 0.081 | 0.523 ± 0.268 | 0.145 ± 0.009 | 0.100 ± 0.024 |
| Kidney | 13.039 ± 3.194 | 16.721 ± 0.992 | 15.526 ± 2.763 | 8.282 ± 1.222 |
| Heart | 0.448 ± 0.056 | 0.290 ± 0.044 | 0.128 ± 0.031 | 0.057 ± 0.010 |
| Lung | 0.621 ± 0.100 | 0.470 ± 0.064 | 0.213 ± 0.008 | 0.112 ± 0.057 |

TABLE 4

Biodistribution of $^{99m}$Tc-MAG$_3$ in rats
(Test group with 20 mg/kg bucolome loading: % dose/organ)

| Organs | 2 minutes | 5 minutes | 10 minutes | 15 minutes |
| --- | --- | --- | --- | --- |
| Spleen | 0.103 ± 0.001 | 0.048 ± 0.006 | 0.018 ± 0.009 | 0.011 ± 0.003 |
| Pancreas | 0.239 ± 0.072 | 0.139 ± 0.030 | 0.060 ± 0.023 | 0.075 ± 0.053 |
| Stomach | 0.289 ± 0.057 | 0.153 ± 0.023 | 0.111 ± 0.032 | 0.104 ± 0.040 |
| Liver | 7.289 ± 0.333 | 3.140 ± 0.745 | 1.217 ± 0.471 | 0.806 ± 0.187 |
| Kidney | 26.404 ± 2.243 | 22.952 ± 9.437 | 17.118 ± 8.295 | 9.544 ± 3.655 |
| Heart | 0.210 ± 0.034 | 0.114 ± 0.019 | 0.037 ± 0.012 | 0.029 ± 0.014 |
| Lung | 0.742 ± 0.044 | 0.456 ± 0.137 | 0.148 ± 0.079 | 0.085 ± 0.025 |
| Urine | 0.802 ± 0.709 | 2.692 ± 2.721 | 14.792 ± 4.307 | 23.969 ± 18.025 |

TABLE 5

Biodistribution of $^{99m}$Tc-MAG$_3$ in rats
(Test group with 20 mg/kg bucolome loading: % dose/g tissue)

| Organs | 2 minutes | 5 minutes | 10 minutes | 15 minutes |
|---|---|---|---|---|
| Blood | 1.050 ± 0.057 | 0.544 ± 0.043 | 0.186 ± 0.076 | 0.152 ± 0.088 |
| Spleen | 0.153 ± 0.018 | 0.083 ± 0.005 | 0.026 ± 0.011 | 0.018 ± 0.006 |
| Pancreas | 0.314 ± 0.013 | 0.145 ± 0.017 | 0.062 ± 0.021 | 0.088 ± 0.052 |
| Stomach | 0.145 ± 0.121 | 0.033 ± 0.017 | 0.033 ± 0.020 | 0.032 ± 0.012 |
| Liver | 0.853 ± 0.135 | 0.280 ± 0.017 | 0.117 ± 0.035 | 0.088 ± 0.028 |
| Kidney | 13.069 ± 0.379 | 11.050 ± 4.260 | 8.558 ± 3.867 | 4.809 ± 1.823 |
| Heart | 0.329 ± 0.034 | 0.172 ± 0.021 | 0.057 ± 0.017 | 0.045 ± 0.021 |
| Lung | 0.613 ± 0.013 | 0.373 ± 0.073 | 0.120 ± 0.049 | 0.081 ± 0.020 |

TABLE 6

Biodistribution of $^{99m}$Tc-MAG$_3$ in rats
10 minutes after the administration
(Test group with 100 mg/kg bucolome loading: % dose/g tissue)

| Organs | Control group | Test group with bucolome loading |
|---|---|---|
| Blood | 0.317 ± 0.073 | 0.047 ± 0.044 |
| Brain | 0.010 ± 0.001 | 0.001 ± 0.001 |
| Spleen | 0.052 ± 0.008 | 0.009 ± 0.008 |
| Pancreas | 0.046 ± 0.000 | 0.006 ± 0.007 |
| Stomach | 0.024 ± 0.024 | 0.040 ± 0.036 |
| Liver | 0.151 ± 0.001 | 0.033 ± 0.026 |
| Kidney | 6.191 ± 0.187 | 0.651 ± 0.324 |
| Heart | 0.101 ± 0.016 | 0.014 ± 0.010 |
| Lung | 0.195 ± 0.030 | 0.043 ± 0.037 |

Example 3

Examination of Displacement Effect on $^{99m}$Tc-MAG$_3$ by Means of Renography in Rats By using Wistar-strain rats (body weight: 400 g), displacement effect of bucolome on $^{99m}$Tc-MAG$_3$ was examined by means of renography in rats. Prism 3000 (picker) was used as an apparatus.

Figure 7:
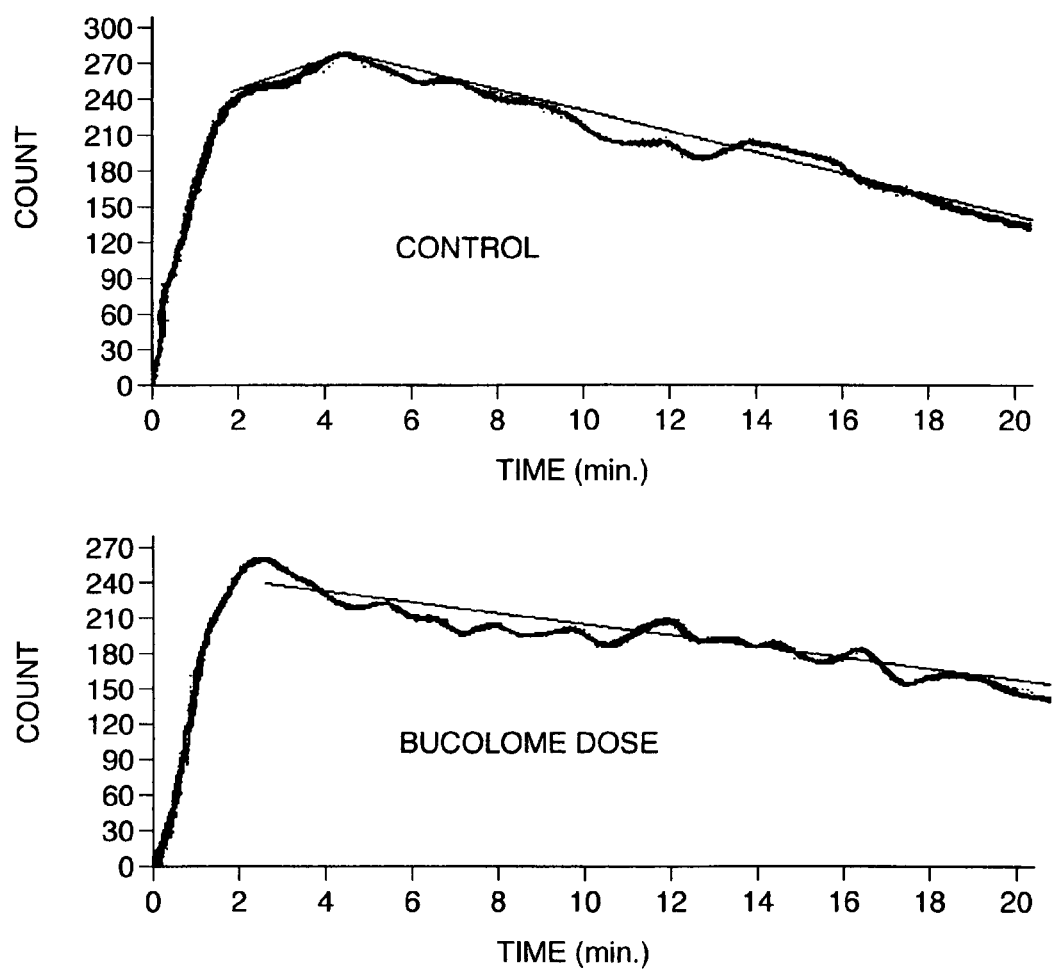
FIG. 7 shows the renogram of $^{99m}$Tc-MAG$_3$ in rat.

A catheter was inserted into the femoral vein of the rat, then $^{99m}$Tc-MAG$_3$ (11.1 MBq) was injected through the catheter and the control renogram was obtained. The dynamic imaging was conducted 10 seconds/scan for 20 minutes. About 2 hours after, confirming the urination and decrease in background radioactivity, then bucolome was loaded to the same rat. Bucolome was dissolved in ethanol and adjusted as in the dose of 20 mg/kg, then intravenously injected by using a microinjector taken in 10 minutes. About 5 minutes after finish of the intravenous injection of bucolome, $^{99m}$Tc-MAG$_3$ was intravenously injected through the catheter and the renogram was taken similarly by 10 seconds/scan for 20 minutes. FIG. 7 shows the renogram (time-radioactivity curves in the kidney) used for functional analysis of the kidney. As can be seen from the FIG. 7, in the control group, the radioactivity curve went up gradually at the initial stage after the administration, and the peak time was 240 seconds. On the other hand, in the test group with bucolome loading, the radioactivity curve rose quickly, and the peak time was 120 seconds which was a half length of that of the control group. Renal function is usually analyzed by determination of the peak time in this renogram and a slope of the straight line in a linear regression. By inhibiting the binding ability of $^{99m}$Tc-MAG$_3$ to plasma protein, the renogram was obtained as close to an ideal and was apploximated to a simple curve. Thus, the functional analysis of the kidney can be easily carried out, and the time for functional analysis can be shortened by shortening the peak time.

TABLE 7

Analytical results of renogram of $^{99m}$Tc-MAG$_3$ in rats

| | Peak time (Second) | Slope (Count/second) |
|---|---|---|
| Rat 1 | | |
| Control group | 240 | 1.166 |
| Test group (with bucolome loading) | 110 | 2.208 |
| Rat 2 | | |
| Control group | 170 | 0.941 |
| Test group (with bucolome loading) | 120 | 2.000 |

Example 4

Examination of Displacement Effects of the Second Drugs On $^{99m}$Tc-EDC Binding to Plasma Protein Displacement experiment of $^{99m}$Tc-ECD binding to a serum albumin was conducted by procedures similar to those shown in Example 1 using human serum; and bucolome, valproic acid, warfarin and cefazolin with binding specificity to the site I on albumin; ibuprofen and sodium octanoate with binding specificity to the site II on alubumin; and etoposide with binding specificity to HAS on which binding site is not identified. The results are shown in Table 8.

As compared with the free fraction (26.03%) of $^{99m}$Tc-ECD in human serum shown in control group, the free fraction of $^{99m}$Tc-ECD in human serum were remarkably increased in test group by etoposide, both at the concentration of 200 μM and 400 μM. Similarly, the free fraction of $^{99m}$Tc-ECD in human serum were also incresed by bucolome, valproic acid and warfarin, but were not remarkably shown as compared with that of etoposide. On the contrary, the free fraction of $^{99m}$Tc-ECD in human serum were not clearly increased by ibuprofen and sodium octanoate which have the specificity to the site II on albumine.

TABLE 8

Displacement of $^{99m}$Tc-ECD binding to plasma protein

| Site-specific drug (second drug) | free fraction of $^{99m}$Tc-ECD (%) | |
|---|---|---|
| Concentration | 200 μM | 400 μM |
| Control | | 26.03% |
| Bucolome | 28.62% | 30.25% |
| Valproic acid | 28.36% | 30.25% |
| Warfarin | 31.00% | 31.37% |
| Cefazolin | 25.92% | 27.40% |
| Etoposide | 33.26% | 37.38% |
| Ibuprofen | 23.09% | 24.09% |
| Octanoic acid | 28.22% | 29.64% |

Example 5

Examination of Displacement Effects of the Second Drugs on $^{123}$I-IMP Binding to Plasma Protein Displacement experiment of $^{123}$I-IMP binding to a serum albumin was conducted by procedures similar to those shown in Example 1 using human serum; and as the second drug, bucolome and warfarin with binding specificity to the binding site I on albumin; ibuprofen, sodium octanoate, 6-methoxy-2-naphthylacetic acid (6-MNA) with binding specificity to the binding site II on alubumin; and verapamil which has the specificity to $\alpha_1$-acid glycoprotein (AGP). Concentration of the second drug (e.g., bucolome) was 400 μM and added amount of $^{123}$I-IMP was about 220 kBq/20 μL. The results are shown in Table 9.

As compared with free fraction (29.29%) of $^{123}$I-IMP in human serum shown in control group, the free fraction of $^{123}$I-IMP in human serum in test group was remarkably incresed by adding verapamil with binding specificity to AGP. Further, the free fraction of $^{123}$I-IMP binding in human serum in test group was also increased by warfarin and 6-MNA mainly bound to albumin. In view of these facts, it is suggested that $^{123}$I-IMP binds to the binding site on both albumin and AGP, and it is clearly understood that the free fraction of $^{123}$I-IMP can be increased by a drug having the specificity to each binding sites of these proteins.

TABLE 9

Displacement of $^{123}$I-IMP binding to human plasma protein (Concentration of the site-specific drug was 400 μM)

| Site-specific drug (second drug) | free of fraction of $^{123}$I-IMP (%) |
|---|---|
| Control | 29.29% |
| bucolome | 30.26% |
| warfarin | 34.69% |
| ibuprofen | 28.43% |
| octanoic acid | 28.74% |
| 6-MNA | 32.70% |
| verapamil | 38.34% |

Example 6

Examination of Displacement Effects of the Second Drugs on $^{123}$I-IMP Binding to Plasma Protein; Synergistic Effect Displacement experiment of $^{123}$I-IMP binding to serum albumin was conducted by procedures similar to those shown in Example 5 using human serum and as the second drugs, 6-MNA having the specificity to the binding site II on albumin and verapamil having the specificity to the binding site on AGP. Concentration of the second drugs were 400 μM and the added amount of $^{123}$I-IMP was about 220 kBq/20 μL.

The tests were conducted in one group by using 6-MNA or verapamil independently, and in another group by using 6-MNA and verapamil simultaneously to study synergistic effect. In both groups, concentrations of the second drugs were 400 μM. The results are shown in Table 10.

In case of using 6-MNA and verapamil simultaneously, the free fraction of $^{123}$I-IMP was over than the sum of the corresponding values obtained by single use of 6-MNA or verapamil, respectively. In view of the above facts, synergistic effect can be expected by using the plural second drugs.

TABLE 10

Displacement of $^{123}$I-IMP binding to human plasma protein: synergistic effect

| Site-specific drug (second drug) | free of fraction of $^{123}$I-IMP (%) |
|---|---|
| Control | 26.52% |
| 6-MNA | 30.00% |
| verapamil | 33.87% |
| 6-MNA + verapamil | 39.26% |

Example 7

Biodistribution of $^{123}$I-IMP in Rat with Verapamil Loading (1) Preparation of $^{123}$I-IMP Verapamil Mixed Solution 35 Milligrams of verapamil bulk drug powder was dissolved in 2 ml of Vasolan injection (verapamil 5 mg/2 ml, manufactured by Eisai Co., Ltd.), then 34 μL of $^{123}$I-IMP injection (111 MBq/ml, manufactured by NIHON MEDI-PHYSICS CO., LTD.) was added thereto and mixed throughly.

(2) Biodistribution of $^{123}$I-IMP in Rats

Control group: $^{123}$I-IMP Injection solution (185 kBq/300 μL) being diluted with physiological saline was administered via the caudal vein of rats of control group. The rats were decapitated at 2, 5, 10, 30 and 60 minutes after administration. Then the blood was sampled and the organs of interest were excised. After measured the weight of these specimens, the radioactivities of the blood and organs were measured. After half-life of the radioactivities were corrected, the accumulation rate (% dose/g of the tissue) was obtained.

Test group: 100 μL of $^{123}$I-IMP verapamil mixed solution was administered via the caudal vein of rats of the test group (about 10 mg/kg loaded as verapamil), then the rats were treated similarly to those of control group. The results of biodistribution of $^{123}$I-IMP are shown in Table 11 (control group), Table 12 (test group with verapamil loading), and Table 13 (comparison of both control and test groups of 10 minutes after the administration).

(3) Examination of Displacement Effect on $^{123}$I-IMP Binding to Plasma Protein in Rat Under the same conditions as mentioned above concerning the constitution of control and testing group, timings of decapitation, and dose of drugs, administrations of the drugs and decapitations of rats were conducted, and 3–5 ml of blood per one rat was sampled. Serum was separated using a sample tube, after that the free fraction of $^{123}$I-IMP was determined by the procedures as described in Example 1. The free fraction of $^{123}$I-IMP in the blood sample of rat obtained at each decapitation timing are shown in Table 14.

As shown in Table 14, it is clearly indicated that the free fraction of $^{123}$I-IMP in the blood sample of rat were increased by the loading with the verapamil. As shown in Table 11 through Table 13, corresponding to increasing in the free fraction of $^{123}$I-IMP in the blood due to the loading with verapamil, the uptake of $^{123}$I-IMP into the brain which is the target organ of $^{123}$I-IMP was rapidly increased after administration of $^{123}$I-IMP-verapamil mixed solution in the test group, thus the brain uptake of $^{123}$I-IMP in the test group after the administration was increased about 2 times higher than that of shown in control group. These facts indicate that, even if a mixed drug of the first drug and the second drug is administered (simultaneous administration of the first drug and the second drug), the free fraction of $^{123}$I-IMP can be regulated by the second drug, and the biodistribution of the first drug could reflect it.

TABLE 13

Biodistribution of $^{123}$I-IMP in rats 10 minutes after the administration (% Dose/g Tissue)

| Tissue | Control group | Test group with verapamil loading |
|---|---|---|
| Blood | 0.116 ± 0.011 | 0.139 ± 0.003 |
| Brain | 1.006 ± 0.379 | 2.145 ± 0.410 |
| Pancreas | 1.721 ± 0.217 | 1.911 ± 0.685 |
| Spleen | 1.008 ± 0.074 | 0.213 ± 0.118 |
| Stomach | 0.407 ± 0.230 | 0.377 ± 0.013 |
| Liver | 0.711 ± 0.143 | 0.688 ± 0.237 |
| Kidney | 1.303 ± 0.190 | 1.766 ± 0.678 |
| Heart | 0.631 ± 0.111 | 1.247 ± 0.209 |
| Lung | 6.279 ± 1.026 | 6.947 ± 1.486 |

TABLE 11

Biodistribution of $^{123}$I-IMP in rats (Control group: % Dose/g Tissue)

| Tissues | 2 minutes | 5 minutes | 10 minutes | 30 minutes | 60 Minutes |
|---|---|---|---|---|---|
| Blood | 0.198 ± 0.052 | 0.133 ± 0.005 | 0.116 ± 0.011 | 0.136 ± 0.028 | 0.181 ± 0.006 |
| Brain | 1.800 ± 0.418 | 1.476 ± 0.225 | 1.006 ± 0.379 | 1.346 ± 0.345 | 1.511 ± 0.011 |
| Pancreas | 1.503 ± 0.353 | 1.923 ± 0.445 | 1.721 ± 0.217 | 2.032 ± 0.505 | 1.957 ± 0.345 |
| Spleen | 0.880 ± 0.216 | 0.999 ± 0.355 | 1.008 ± 0.074 | 1.356 ± 0.277 | 1.290 ± 0.138 |
| Stomach | 0.302 ± 0.065 | 0.500 ± 0.078 | 0.407 ± 0.230 | 0.885 ± 0.366 | 1.245 ± 0.343 |
| Liver | 0.506 ± 0.109 | 0.699 ± 0.061 | 0.711 ± 0.143 | 1.192 ± 0.536 | 1.442 ± 0.164 |
| Kidney | 3.406 ± 0.905 | 2.285 ± 0.256 | 1.303 ± 0.190 | 1.359 ± 0.222 | 1.585 ± 0.132 |
| Heart | 1.949 ± 0.293 | 1.014 ± 0.070 | 0.631 ± 0.111 | 0.524 ± 0.037 | 0.540 ± 0.026 |
| Lung | 11.236 ± 0.780 | 9.000 ± 0.600 | 6.279 ± 1.026 | 5.209 ± 1.446 | 5.186 ± 0.616 |

TABLE 12

Biodistribution of $^{123}$I-IMP in rats [Test group: (Loaded with verapamil): % Dose/g Tissue]

| Tissues | 2 minutes | 5 minutes | 10 minutes | 30 minutes | 60 Minutes |
|---|---|---|---|---|---|
| Blood | 0.238 ± 0.083 | 0.228 ± 0.012 | 0.139 ± 0.003 | 0.098 ± 0.044 | 0.110 ± 0.002 |
| Brain | 1.584 ± 0.425 | 1.916 ± 0.131 | 2.145 ± 0.410 | 1.529 ± 0.811 | 1.449 ± 0.281 |
| Pancreas | 1.268 ± 0.375 | 1.659 ± 0.496 | 1.911 ± 0.685 | 1.877 ± 0.886 | 1.478 ± 0.161 |
| Spleen | 0.052 ± 0.025 | 0.063 ± 0.250 | 0.213 ± 0.118 | 0.886 ± 0.319 | 1.193 ± 0.129 |
| Stomach | 0.234 ± 0.111 | 0.164 ± 0.078 | 0.377 ± 0.013 | 0.782 ± 0.621 | 1.058 ± 0.126 |
| Liver | 0.287 ± 0.156 | 0.350 ± 0.130 | 0.688 ± 0.237 | 1.185 ± 0.751 | 1.639 ± 0.051 |
| Kidney | 1.424 ± 0.313 | 1.278 ± 0.381 | 1.766 ± 0.678 | 1.231 ± 0.632 | 1.242 ± 0.146 |
| Heart | 3.769 ± 0.911 | 2.260 ± 0.680 | 1.247 ± 0.209 | 0.471 ± 0.209 | 0.456 ± 0.039 |
| Lung | 9.234 ± 1.748 | 8.377 ± 0.563 | 6.947 ± 1.486 | 3.890 ± 2.223 | 4.133 ± 0.079 |

TABLE 14

Free fraction (%) of $^{123}$I-IMP in the blood of rats

| Tissues | 2 minutes | 5 minutes | 10 minutes | 30 minutes | 60 Minutes |
|---|---|---|---|---|---|
| Control group | 56.75 ± 9.21 | 50.70 ± 10.37 | 45.91 ± 3.12 | 27.29 ± 4.85 | 16.77 ± 4.11 |
| Test group with verapamil loading | 52.40 ± 6.00 | 56.52 ± 4.38 | 66.86 ± 6.34 | 38.03 ± 6.69 | 31.86 ± 8.23 |

Example 8

Examination of regulating the free fraction of $^{125}$I-FP-CIT

Experiment was conducted by procedures similar to those shown in Example 5 using human serum and as the second drug, bucolome, phenylbutazone, warfarin and dansyl-L-asparagine (DNSA) with binding specificity to the binding site I on albumin, and ibuprofen, 6-methoxy-2-naphthylacetic acid (6-MNA) with binding specificity to the binding site II on albumin. Concentration of the second drug (e.g., bucolome and the like) were 400 μM and added amount of $^{123}$I-FP-CIT was about 74 kBq/20 μL. The result are shown in Table 15.

As compared with the free fraction (17.26%) of $^{123}$I-FP-CIT in human serum shown in control group, the free fraction of $^{123}$I-FP-CIT in test group was remarkably decreased by DNSA. Furthermore, the free fraction of $^{123}$I-FP-CIT in test group was also decreased by phenylbutazone and ibuprofen. In view of these facts, it is clearly understood that the free fraction of the first drug can be decreased by the second drug having the binding affinity for the plasma proteins.

TABLE 15

Free fraction of $^{123}$I-FP-CIT in human serum (concentration of the site-specific drug was 400 μM)

| Site-specific drug (second drug) | free fraction (%) of $^{123}$I-FP-CIT |
|---|---|
| Control | 17.26% |
| bucolome | 18.40% |
| phenylbutazone | 14.92% |
| warfarin | 17.88% |
| DNSA | 12.80% |
| ibuprofe | 15.92% |
| 6-MNA | 18.10% |

The invention claimed is:

1. Method of in-vivo administration of drugs with binding affinity for plasma protein, which is characterized in that, in the administration of a first drug with binding affinity for plasma protein, verapamil as a second drug with binding affinity for the same plasma protein for which the first drug has binding affinity, is administered simultaneously with the first drug or before or after the administration of the first drug to thereby regulate the binding of the first drug to the plasma protein.

2. The method of the administration of drugs with binding affinity for plasma protein according to claim 1, wherein the second drug has binding affinity to the same binding sites on plasma protein to which the first drug has binding affinity.

3. The method of the administration of drug with binding affinity for plasma protein according to claim 1, wherein the first drug is a radiodiagnostic drug for in vivo use or a radiotherapeutic drug for in vivo use.

4. The method of the administration of drugs with binding affinity for plasma protein according to claim 2, wherein the first drug is a radiodiagnostic drug for in vivo use or a radiotherapeutic drug for in vivo use.

5. The method of the administration of drugs with binding affinity for plasma protein according to claim 3 or 4, wherein the radiodiagnostic drug for in vivo use or the radiotherapeutic drug for in vivo use is radiolabeled with one nuclide selected from the group consisting of 11-carbon ($^{11}$C), 15-oxygen ($^{15}$O), 18-fluorine ($^{18}$F), 32-phosphorus ($^{32}$P), 59-iron ($^{59}$Fe), 67-copper ($^{67}$Cu), 67-gallium ($^{67}$Ga), 81m-krypton ($^{81m}$Kr), 81-rubidium ($^{81}$Rb), 89-strontium ($^{89}$Sr), 90-yttrium ($^{90}$Y), 99m-technetium ($^{99m}$Tc), 111-indium ($^{111}$In), 123-iodine ($^{123}$I), 125-iodine ($^{125}$I), 131-iodine ($^{131}$I), 133-xenon ($^{133}$Xe), 117m-tin ($^{117m}$Sn), 153-samarium ($^{153}$Sm), 186-rhenium ($^{186}$Re), 188-rhenium ($^{188}$Re), 201-thallium ($^{201}$Tl), 212-bismuth ($^{212}$Bi), 213-bismuth ($^{213}$Bi) and 211-astatine ($^{211}$At).

6. The method of the administration of drugs with binding affinity for plasma protein according to claim 3 or 4, wherein the first drug has one group labeled with nuclide and the group is selected from the group consisting of a bisaminothiol compound, a monaminomonoamidobisthiol compound, a bisamidobisthiol compound, a mercaptoacetylglycylglycylglycine compound, a hexamethylpropyleneamineoxime compound, an ethylenebis [bis(2-ethoxyethyl) phosphine] compound, a 2,3-dimercaptosuccinic acid compound, an ethylenecysteine dimer compound, a methoxyisobutylisonitrile compound, a polyamine compound, a pyriodoxyldeneaminate compound, methylene diphosphonate, a hydroxymethylene diphosphonate compound, a β-methyl-ω-phenylpentadecanoic acid compound, N-isopropylamphetamine, hippuric acid, benzylguanidine and a tropane compound.

7. A pharmaceutical preparation for regulating binding affinity of a first drug for plasma protein, which comprises a first drug with binding affinity for plasma protein and verapamil as a second drug with binding affinity for the same plasma protein, for which the first drug has binding affinity.

8. The pharmaceutical preparation according to claim 7, wherein each of the first drug and the second drug is in a separate container, and prepared as a kit.

9. The pharmaceutical preparation according to claim 7, wherein the second drug has binding affinity to the same binding sites on the plasma protein, to which the first drug has binding affinity.

10. The pharmaceutical preparation according to claim 8, wherein the second drug has binding affinity to the same binding sites on the plasma protein, to which the first drug has binding affinity.

11. The pharmaceutical preparation according to any one of claims 7 to 10, wherein the first drug is a radiodiagnostic drug for in vivo use or a radiotherapeutic drug for in vivo use.

12. The pharmaceutical preparation according to claim 11, wherein the radiodiagnostic drug for in vivo use or the radiotherapeutic drug for in vivo use is radiolabeled with one nuclide selected from the group consisting of 11-carbon ($^{11}$C), 15-oxygen ($^{15}$O), 18-fluorine ($^{18}$F), 32-phosphorus ($^{32}$P), 59-iron ($^{59}$Fe), 67-copper ($^{67}$Cu), 67-gallium ($^{67}$Ga), 81m-krypton ($^{81m}$Kr), 81-rubidium ($^{81}$Rb), 89-strontium ($^{89}$Sr), 90-yttrium ($^{90}$Y), 99m-technetium ($^{99m}$Tc), 111-indium ($^{111}$In), 123-iodine ($^{123}$I), 125-iodine ($^{125}$I), 131-iodine ($^{131}$I), 133-xenon ($^{133}$Xe), 117m-tin ($^{117m}$Sn), 153-samarium ($^{153}$Sm), 186-rhenium ($^{186}$Re), 188-rhenium ($^{188}$Re), 201-thallium ($^{201}$Tl), 212-bismuth ($^{212}$Bi), 213-bismuth ($^{213}$Bi) and 211-astatine ($^{211}$At).

13. The pharmaceutical preparation according to claim 11, wherein the first drug has one group labeled with nuclide and the group is selected from the group consisting of a bisaminothiol compound, a monaminomonoamidobisthiol compound, a bisamidobisthiol compound, a mercaptoacetylglycylglycylglycine compound, a hexamethylpropyleneamineoxime compound, an ethylenebis [bis(2-ethoxyethyl) phosphine] compound, a 2,3-dimercaptosuccinic acid compound, an ethylenecysteine dimer compound, a methoxyisobutylisonitrile compound, a polyamine compound, a pyriodoxylydeneaminate compound, methylene diphosphonate, a hydroxymethylene diphosphonate compound, a β-methyl-ω-phenylpentadecanoic acid compound, N-isopropylamphetamine, hippuric acid, benzylguanidine and a tropane compound.

* * * * *